United States Patent [19]

Tursz et al.

[11] Patent Number: 5,358,709

[45] Date of Patent: Oct. 25, 1994

[54] ANTITUMORAL COMPOSITION BASED ON POLYPEPTIDES HAVING HUMAN INTERLEUKIN 2 ACTIVITY

[75] Inventors: Thomas Tursz, Cedex; Maud Brandely, Paris, both of France

[73] Assignee: Roussel Uclaf, France

[21] Appl. No.: 867,114

[22] PCT Filed: Dec. 27, 1990

[86] PCT No.: PCT/FR90/00951

§ 371 Date: Jul. 8, 1992

§ 102(e) Date: Jul. 8, 1992

[87] PCT Pub. No.: WO92/07577

PCT Pub. Date: May 14, 1992

[30] Foreign Application Priority Data

Oct. 30, 1990 [FR] France .................................. 90 13441

[51] Int. Cl.$^5$ .............................................. A61K 45/05
[52] U.S. Cl. ................................................ 424/85.2
[58] Field of Search ..................................... 424/85.2

[56] References Cited

PUBLICATIONS

Berthaud et al, The Lancet, vol. 335 (8705) Jun. 30, 1990, p. 1590.
Hsu et al, Biol. Abst. 89(6) #60857, 15 Mar. 1990, p. AB-623.
Kolitz et al, J. Biol. Resp. Mod., vol. 6, No. 4. 1987 Raven Press, pp. 412–429.
Ju et al., J. Biol. Chem. vol. 262, No. 12, Apr. 25, 1987, pp. 5723–5731.
Taniguchi et al, Nature, vol. 302, Mar. 24, 1983 pp. 305–310.

*Primary Examiner*—Michael G. Wityshyn
*Assistant Examiner*—C. Sayala
*Attorney, Agent, or Firm*—Bierman and Muserlian

[57] ABSTRACT

The use of a polypeptide having human interleukin 2 activity for preparing a pharmaceutical composition for treating malignant epithelial tumours of the upper respiratory/alimentary tract or the thymus, is described.

9 Claims, No Drawings

ANTITUMORAL COMPOSITION BASED ON POLYPEPTIDES HAVING HUMAN INTERLEUKIN 2 ACTIVITY

The present invention relates to the use of a polypeptide having the activity of human interleukin 2 for the preparation of pharmaceutical compositions intended for the treatment of epithelial malignant tumours.

Interleukin 2 ($IL_2$) which is a lymphokine produced by activated T lymphocytes possesses an immunomodulatory activity and an anti-tumour activity described for example by Fletcher, M et al. (Lymphokine Research 6 1987 47–57), which activities include in particular the ability to initiate the proliferation of the T lymphocyctes and the induction of the cytotoxicity of the NK (natural killer) cells and the LAK (lymphokine activated killer) cells. It has been observed that the administration of $IL_2$ either on its own at a high dose or combined with LAK cells is able to induce the regression of certain cancers present in a mouse and in patients having metastatic cancers such as melanoma, cancer of the kidney, colorectal cancer or non-Hodgkin's lymphoma (Rosenberg, S A et al. N. Engl. J. Med. 1987 316 889–897).

Malignant epithelial tumours, or epitheliomas, which are tumours caused by a neoplasic proliferation of the epithelial cells or epidermis, or epidermoid mucous membranes, are histologically diagnosed, in particular in the upper aerodigestive tracts or in the thymus.

The epitheliomas of the upper aerodigestive tracts concern the various sites of the pharynx, amongst which the nasopharynx which represents a relatively frequent localization with different histological sub-types, most often of lymphoepithelial type characterized by an undifferentiated epithelioma infiltrated by lymphocytes.

The most important treatment of epitheliomas is radiotherapy, generally preceded by polychemotherapy or combined with the latter. The prognosis, variable according to the development of the epithelioma, is unfavourable in as much as a large percentage of patients treated develop metastases afterwards. Thus a study involving 49 patients suffering from carcinomas of the nasopharynx and treated by radio-therapy, either on its own or preceded by chemotherapy, describes an average survival rate of 42% after 5 years (Stein, M et al. J. Surg. Oncol. 1988 37 (2) 84–88). In spite of a prognosis which seems better when lymphoepitheliomas are concerned, a low survival rate of only 13% is observed after 5 years in a study involving 150 patients suffering from nasopharyngeal carcinoma, most frequently of lymphoepithelial type, although a complete remission rate of about 65% was described after radiotherapy preceded or not preceded by chemotherapy (Koppibar, S B et al. J. Surg. Oncol. 1988 39 (3) 179–182). The absence of an effective treatment is also recognized, notably in 29 children all suffering from lymphoepitheliomas of the nasopharynx, amongst which more than 50% developed secondary metastases within 2 years once the radiotherapy had stopped (Pao, W J et al. In. J. Radiat. Oncol. Biol. Phys 1989 17 (2) 299–305).

Malignant thymomas which are tumours of the thymus caused by a neoplastic proliferation of the epithelial cells of the thymus include mainly invasive malignant thymomas without atypia, amongst which there can possibly be singled out the lymphoepithelial or lymphocytary sub-type according to the cell population which accompanies them, and the atypical carcinomas of the thymus.

In contrast to benign encapsulated thymomas for which suitable treatments exist such as surgery, radiotherapy, alone or combined, malignant thymomas, in particular invasive malignant thymomas without atypia, are not very sensitive to conventional treatments. Furthermore, the frequency with which they appear is increasing (23 to 66% of all thymomas).

Thus invasive malignant thymomas treated either by surgery, or by radiotherapy as the first treatment, followed optionally by chemotherapy, have an unfavourable prognosis: up to 30% of the patients secondarily develop metastases. The results described for patients suffering from lymphoepithelial thymomas (Arriagada, R et al. Eur J Cancer Clin Oncol 20 (No. 1) 69–74 1984) or for patients suffering from lympho-epithelial or lymphocytary thymomas (Goldel, N et al. Cancer 63 1493–1500 Apr. 15 1989) are deceptive with the exception of a few encouraging results described after treatment by polychemotherapy of invasive malignant thymomas rich in undifferentiated epithelial cells (Dy, C et al. Journal of Clinical Oncology 6 (No. 3) 536–542 March 1988). Therefore no recognized treatment exists, in particular for the invasive forms of malignant thymomas or for atypical carcinomas of the thymus for which high rates of resistant cases are observed, in particular to chemotherapy.

No clinical result has described the use of $IL_2$ in the treatment of epithelial tumours of the upper aerodisgestive tracts.

A clinical result has shown the ineffectiveness of the therapy in malignant thymomas with $IL_2$ on its own, notably with a mutein of $IL_2$ in a patient suffering from thymoma having received a dose of $1 \times 10^6$ U/M$^2$ by intravenous route perfused over 6 hours according to a cycle constituted by 2 times 5 days (Kolitz, J E et al. Journal of Biological Response Modifiers 6 412–429 1987).

Now in a surprising way, the Applicant has just obtained results showing that $IL_2$ on its own has an activity on epitheliomas.

Therefore the invention relates to the use of a polypeptide having the activity of human interleukin 2 for preparing a pharmaceutical composition intended for the treatment of epithelial malignant tumours of the upper aerodigestive tracts or of the thymus.

By polypeptide having the activity of human $IL_2$ is meant natural human $IL_2$, recombinant human $IL_2$, that is obtained by the technology of recombinant DNA, for example such as that described by Taniguchi, T et al. Nature 1983 302 305–310 or in the Patent EP 91530 B, alleles or derivatives of these products as described for example by Ju, C et al. J. Biol. Chem. 1987 262 5723–5731.

The tumours of the upper aerodigestive routes with which the invention is concerned include epitheliomas of the pharynx in general, for example epitheliomas of the nasopharynx, of the tonsils or of the oesophagus. The tumours of the thymus with which the invention is concerned include epithelial, lymphoepithelial or lymphocytary invasive malignant thymoma and carcinomas of the thymus.

Notably a subject of the invention is the use characterized in that the tumour of the upper aerodigestive tracts is a lymphoepithelioma, histologically diagnosed.

Also a subject of the invention is the use characterized in that the tumour of the thymus is a lymphoepithelial invasive malignant thymoma, diagnosed by the usual histological, cytological and biological examinations. The use according to the invention is intended for the treatment of malignant thymoma, for the treatment of the recurrence of the latter or for its preventative treatment.

The use of $IL_2$ according to the invention is illustrated by a partial response in a patient suffering from malignant thymoma having undergone, without success, a previous chemotherapy treatment.

A particular subject of the invention is the use characterized in that the human $IL_2$ is a pure recombinant $IL_2$.

The pharmaceutical compositions prepared according to the invention contain a recombinant human $IL_2$, alleles or derivatives of the latter, as described above, for which purification techniques known to a man skilled in the art are used, which allow the preparation of pure products.

A more particular subject of the invention is the use characterized in that the $IL_2$ is a non-glycosylated recombinant $IL_2$ in reduced form. The non-glycosylated $IL_2$ used is notably that having the sequence of natural $IL_2$ with 133 aminoacids, optionally with an additional N-terminal methionin, of which the 3 cysteines in position 58, 105 and 125 are in reduced form, showing a biological activity comparable to that of oxidized $IL_2$ having the same sequence containing a disulphide bridge in position 58-105 and which is described in the European Patent Application EP 0353150. By reduced form is meant that the cysteine remainders contained by the $IL_2$ comprise a free sulphhydryl group the determination of which is made, for example, by spectrophotometry with dithiodipyridine as the reagent of the thiols. The biological activity is determined by measuring the proliferation of leukemic cell lines of $IL_2$ CTLL-2 dependent mice, with a colorimetric test using a tetrazolium salt (Mossman, T J Immunol. Meth 1983 65 55–63). The specific activity of the recombinant $IL_2$'s used in the invention is at least equal to $0.5 \times 10^7$ U BRMP/mg, preferably $1 \times 10^7$ U BRMP/mg. The $IL_2$ activity unit is defined as the quantity which produces 50% of the maximum response in the test. A "Biological Response Modifier Program" (BRMP), reference agent human $IL_2$ "jurkat" sample provided by the National Cancer Institute (NCI) is used as standard.

A subject of the invention is especially the use characterized in that $IL_2$ is administered by intravenous route as a continuous perfusion at a dose of 2 to $25 \times 10^6$ U/$M^2$ per day and more especially that characterized in that $IL_2$ is administered at a dose of $20 \times 10^6$ U/$M^2$ per day.

A subject of the invention is quite especially the use characterized in that $IL_2$ is administered in a cycle of 3 to 5 consecutive days and characterized in that $IL_2$ is administered repeatedly for at least 3 non-consecutive cycles.

The dose administered, the frequency of the injection and the duration of the treatment vary as a function of the condition of the patient.

The $IL_2$ is contained in a pharmaceutical composition, preferably lyophilized in a dosage bottle containing 0.05 to 2 mg of active ingredient and which is reconstituted with distilled water for injection. The solution obtained is immediately diluted with a solute, for example 5% glucose, for administration as an intravenous perfusion.

According to the preferred use of the invention, the $IL_2$ is the reduced recombinant $IL_2$ above, an example of the pharmaceutical preparation of which is given further on, the dose is $20 \times 10^6$ U/$M^2$ per day, according to a cycle of 3 to 5 consecutive days, the duration of administration is 3 non-consecutive cycles as a continuous perfusion by intravenous route.

All the publications which are mentioned are incorporated in the text of the present Application for reference.

The following examples illustrate the invention without however limiting it:

EXAMPLE 1

Pharmaceutical Composition for Perfusion

A preparation for injection by intravenous route as a perfusion is made of formula:

| | |
|---|---|
| reduced $IL_2$ | 0.5 mg |
| citric acid | 5 mg |
| mannitol | 50 mg |
| sterilized water | 1 ml |
| 5% glucose | 50 ml |

EXAMPLE 2

Clinical Study in the Treatment of a Malignant Thymoma

The study includes a patient having a lymphoepithelial malignant thymoma histologically confirmed invading the mediastinum, the right lung, the pleura, the pericardium and the diaphragm, having received a first course of treatment with 2 cycles of conventional polychemotherapy comprising cisplatin, endoxan and vindesine, then a second course of treatment with a high dose (100 mg/$M^2$) of adriamycin without a regression of the tumour having been observed.

The absence, under chemotherapy, of a regression of the mediastinal and pleuropulmonary masses shown by radiography and the thorax scanner, lead to the initiation of a treatment by $IL_2$ four and a half months after this chemotherapy was completed.

The compositions of $IL_2$ prepared according to the invention permit a dose of $20 \times 10^6$ U/$M^2$ per day to be injected as a continuous perfusion by intravenous route for 3 to 5 consecutive days according to a first cycle of 5 days, a second cycle of 4 days and a third cycle of 3 days with an interval of 9 days between each cycle. The tumourous lesions of the patient are evaluated before and after each cycle by radiography then by scanning. The compositions described in Example 1 are used.

The treatment with $IL_2$ brought about a partial response at the level of the pleural masses which decreased by more than 75%, observed by radiography and confirmed by a thorax scanner, without modification of the thymic mass. A thoracotomy is carried out during the course of the treatment with $IL_2$ to check the condition of the thymic sheath. The residual tumourous mass can be completely removed by a surgeon and is found to be massively necrotic whereas the complete removal of the residual metastases at a pulmonary and diaphragmatic level is not technically possible.

We claim:

1. A method of treating an epithelial malignant tumor of the upper aerodigestive tract or of the thymus of a warm-blooded animal comprising administering to said warm-blooded animal an antitumorally effective amount of interleukin 2.

2. The method of claim 1 wherein the tumor is a lymphoepithelioman.

3. The method of claim 1 wherein the tumor is a lymphoepithelial invasive malignant thymona.

4. The method of claim 1 wherein the interleukin 2 is a pure recombinant IL-2.

5. The method of claim 4 wherein the interleukin 2 is non-glycosylated recombinant IL-2 in reduced form.

6. The method of claim 5 wherein the interleukin 2 is administered intravenously by continuous perfusion at a dose of 2 to $25 \times 10^6$ U/M² per day.

7. The method of claim 6 wherein the dose is $20 \times 10^6$ U/M² per day.

8. The method of claim 7 wherein the administration is in a cycle of 3 to 5 consecutive days.

9. The method of claim 8 wherein the administration is repeated for at least 3 non-consecutive days.

* * * * *